United States Patent [19]

Brooks et al.

[11] Patent Number: 5,714,488
[45] Date of Patent: Feb. 3, 1998

[54] BIS-HETEROARYLYLMETHOXYPHENYL KETONE DERIVATIVES AS INHIBITORS OF LEUKOTRIENE BIOSYNTHESIS

[75] Inventors: Clint D. W. Brooks; Pramila Bhatia, both of Libertyville; Teodozyj Kolasa, Lake Villa, all of Ill.

[73] Assignee: Abbott Laboratories, Abbott Park, Ill.

[21] Appl. No.: 703,440

[22] Filed: Sep. 17, 1996

Related U.S. Application Data

[60] Provisional application No. 60/004,707 Oct. 3, 1995.

[51] Int. Cl.[6] .................. C07D 215/14; C07D 215/18; A61K 31/47
[52] U.S. Cl. .............. 514/249; 514/256; 514/314; 514/332; 546/167; 546/173; 546/176; 546/180; 546/181; 546/254; 546/264; 546/266; 544/296; 544/353; 544/356
[58] Field of Search ..................... 514/249, 256, 514/314, 332; 546/167, 173, 176, 180, 181, 254, 264, 266; 544/296, 353, 356

[56] References Cited

U.S. PATENT DOCUMENTS

| | | | |
|---|---|---|---|
| 4,642,347 | 2/1987 | Kreft | 546/181 |
| 4,970,215 | 11/1990 | Mohrs et al. | 514/311 |
| 4,992,576 | 2/1991 | Gapinski | 560/52 |
| 5,326,883 | 7/1994 | Brooks et al. | 549/65 |
| 5,358,955 | 10/1994 | Brooks et al. | 514/311 |
| 5,399,699 | 3/1995 | Kolasa | 546/174 |

FOREIGN PATENT DOCUMENTS

| | | |
|---|---|---|
| A 349 062 | 3/1990 | European Pat. Off. . |
| 0480717 | 4/1992 | European Pat. Off. . |
| WO 94/27968 | 12/1994 | WIPO . |

OTHER PUBLICATIONS

Prasit, et al., Biorganic and Medicinal Chemistry Letters, 1 (11), (1991), 645–648.

Musser, J.H., and Kraft, A.F., Journal of Medicinal Chemistry, 35 (14), 1 (1992), pp. 2501–2523.

*Primary Examiner*—C. Warren Ivy
*Assistant Examiner*—D. Margaret M. Mach
*Attorney, Agent, or Firm*—Frank Z. Yang

[57] ABSTRACT

Compounds having the formula

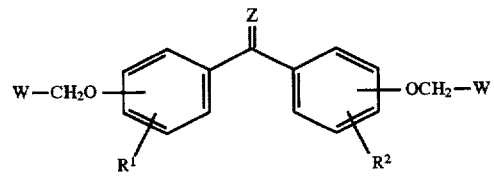

or a pharmaceutically acceptable salt thereof wherein W is selected from the group consisting of optionally substituted quinolyl, optionally substituted benzothiazolyl, optionally substituted benzoxazolyl, optionally substituted benzimidazolyl, optionally substituted quinoxalyl, optionally substituted pyridyl, optionally substituted pyrimidyl, and optionally substituted thiazolyl; $R^1$ and $R^2$ are one or more groups independently selected from hydrogen, alkyl, halolalkyl, alkoxy, and halogen; Z is selected from the group consisting of N—OH, N—O—A—COM, CH—COM, and CH—CH=N—O—A—COM wherein A is selected from the group consisting of alkylene, alkenylene, cycloalkylene, and optionally substituted alkylphenyl wherein the alkyl portion is of one to six carbon atoms, and M is selected from the group consisting of a pharmaceutically acceptable, metabolically clearable group, —$OR^3$, and —$NR^4R^5$, inhibit leukotriene biosynthesis and are useful in the treatment of allergic and inflammatory disease states. Also disclosed are leukotriene biosynthesis inhibiting compositions and a method of inhibiting leukotriene biosynthesis.

10 Claims, No Drawings

BIS-HETEROARYLYLMETHOXYPHENYL KETONE DERIVATIVES AS INHIBITORS OF LEUKOTRIENE BIOSYNTHESIS

CROSS REFERENCE TO RELATED APPLICATIONS

This application claims the benefit of U.S. Provisional application Ser. No. 60/004,707, filed Oct. 3, 1995.

TECHNICAL FIELD

This invention relates to compounds having activity to inhibit leukotriene effects, to pharmaceutical compositions comprising these compounds, and to a medical method of treatment. More particularly, this invention concerns symmetrical oxime ether alkylcarboxylate compounds and derivatives which inhibit leukotriene effects, to pharmaceutical compositions comprising these compounds and to a method of inhibiting leukotriene biosynthesis.

BACKGROUND OF THE INVENTION

The leukotrienes are extremely potent substances which produce a wide variety of biological effects, often in the nanomolar to picomolar concentration range. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important pathophysiological role.

U.S. Pat. No. 4,992,576 (Feb. 21, 1991) discloses benzophenone analogs which inhibit leukotriene biosynthesis.

U.S. Pat. No. 5,358,955 (Oct. 25, 1994) discloses aryl and heteroarylmethoxyphenyl compounds which inhibit leukotriene biosynthesis.

U.S. Pat. No. 4,970,215 (Nov. 13, 1990) discloses quinolylmethoxyphenyl acetic acid derivatives which inhibit leukotriene biosynthesis.

U.S. Pat. No. 5,326,883 (Jul. 5, 1994) discloses oxime ether derivatives having lipoxygenase inhibitory activity.

European Patent Application Number 349 062 (Jan. 3, 1990) discloses quinolylmethoxyphenyl alkanoic acid derivatives which inhibit leukotriene biosynthesis.

European Patent Application Number 480 717 (Apr. 15, 1992) discloses unsaturated hydroxyquinoline acids as leukotriene antagonists.

PCT application Ser. No. WO 94/27968 (Dec. 8, 1994) discloses quinoline derivatives as leukotriene antagonism.

Prasit, et al., *Bioorganic and Medicinal Chemistry Letters*, 1 (11), 645 (1991) describe ((4-(4-chlorophenyl)-1-(4-(2-quinolylmethoxy)phenyl)butyl)thio)acetic acid as an orally active leukotriene biosynthesis inhibitor, and Musser and Kraft, *Journal of Medicinal Chemistry*, 35 (14), 1, (1992) review quinoline containing leukotriene biosynthesis inhibitors.

SUMMARY OF THE INVENTION

In its principal embodiment the present invention provides certain symmetrical carboxylate compounds and their derivatives and pharmaceutically acceptable salts where the compounds are of formula:

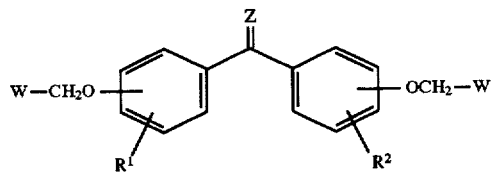

or a pharmaceutically acceptable salt thereof wherein W is the same at each occurrence and is selected from the group consisting of (a) quinolyl; (b) quinolyl substituted with (b-1) halogen, (b-2) alkyl of one to six carbon atoms, (b-3) phenyl, (b-4) phenyl substituted with a substituent selected from the group consisting of (b-4-a) halogen, (b-4-b) alkyl of one to six carbon atoms, (b-4-c) haloalkyl of one to six carbon atoms, and (b-4-d) alkoxy of one to six carbon atoms; (b-5) pyridyl; and (b-6) pyridyl substituted with a substituent selected from the group consisting of (b-6-a) halogen, (b-6-b) alkyl of one to six carbon atoms, and (b-6-c) alkoxy of one to six carbon atoms; (c) benzothiazolyl; (d) benzothiazolyl substituted with a substituent selected from the group consisting of (d-1) halogen, (d-2) alkyl of one to six carbon atoms, (d-3) phenyl, (d-4) phenyl substituted with a substituent selected from the group consisting of (d-4-a) halogen, (d-4-b) alkyl of one to six carbon atoms, (d-4-c) haloalkyl of one to six carbon atoms, and (d-4-d) alkoxy of one to six carbon atoms, (d-5) pyridyl; (d-6) pyridyl substituted with a substituent selected from the group consisting of (d-6-a) halogen, (d-6-b) alkyl of one to six carbon atoms, and (d-6-c) alkoxy of one to six carbon atoms; (e) benzoxazolyl; (f) benzoxazolyl substituted with a substituent selected from the group consisting of (f-1) halogen and (f-2) alkyl of one to six carbon atoms; (g) benzimidazolyl; (h) benzimidazolyl substituted with a substituent selected from the group consisting of (h-1) halogen, and (h-2) alkyl of one to six carbon atoms; (i) quinoxalyl; (j) quinoxalyl substituted with a substituent selected from the group consisting of (j-1) halogen and (j-2) alkyl of one to six carbon atoms; (k) pyridyl; (l) pyridyl substituted with a substituent selected from the group consisting of (l-1) phenyl, (l-2) phenyl substituted with a substituent selected from the group consisting of (l-2-a) halogen, (l-2-b) alkyl of one to six carbon atoms, (l-2-c) haloalkyl of one to six carbon atoms, and (l-2-d) alkoxy of one to six carbon atoms, (l-3) pyridyl, and (l-4) pyridyl substituted with a substituent selected from the group consisting of (l-4-a) halogen, (l-4-b) alkyl of one to six carbon atoms, and (l-4-c) alkoxy of one to six carbon atoms; (m) pyrimidyl; (n) pyrimidyl substituted with a substituent selected from the group consisting of (m-1) phenyl, (m-2) phenyl substituted with a substituent selected from the group consisting of (m-2-a) halogen, (m-2-b) alkyl of one to six carbon atoms, (m-2-c) haloalkyl of one to six carbon atoms, and (m-2-d) alkoxy of one to six carbon atoms, (m-3) pyridyl, and (m-4) pyridyl substituted with a substituent selected from the group consisting of (m-4-a) halogen, m-4-b) alkyl of one to six carbon atoms, and (m-4-c) alkoxy of one to six carbon atoms; (o) thiazolyl, and (p) thiazolyl substituted with a substituent selected from the group consisting of (p-1) phenyl, (p-2) phenyl substituted with a substituent selected from the group consisting of (p-2-a) halogen, (p-2-b) alkyl of one to six carbon atoms, (p-2-c) haloalkyl of one to six carbon atoms, and (p-2-d) alkoxy of one to six carbon atoms, (p-3) pyridyl, or (p-4) pyridyl substituted with a substituent selected from the group consisting of (p-4-a) halogen, (p-4-b) alkyl of one to six carbon atoms, and (p-4-c) alkoxy of one to six carbon atoms.

$R^1$ and $R^2$ are independently selected from the group consisting of (a) hydrogen, (b) alkyl of one to six carbon atoms, (c) halolalkyl of one to six carbon atoms, (d) alkoxy of one to six carbon atoms, and (e) halogen.

Z is selected from the group consisting of (a) N—OH, (b) N—O—A—COM, (c) CH—COM, and (d) CH—CH=N—O—A—COM.

The group A is selected from the group consisting of (a) alkylene of one to six carbon atoms, (b) alkenylene of two to six carbon atoms, (c) cycloalkylene of three to eight carbon atoms, (d)

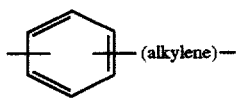

wherein the alkylene portion is of one to six carbon atoms, (e)

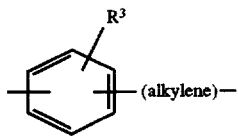

wherein the alkylene portion is of one to six carbon atoms, and $R^3$ is selected from the group consisting of halogen, alkyl of one to six carbon atoms, and haloalkyl of one to six carbon atoms, (f)

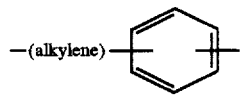

wherein the alkylene portion is of one to six carbon atoms, and (g)

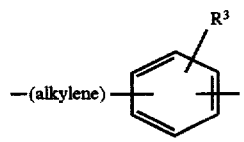

wherein the alkylene portion is of one to six carbon atoms and $R^3$ is as defined above.

M is selected from the group consisting of (a) a pharmaceutically acceptable cation, (b) a pharmaceutically acceptable metabolically clearable group, (c) —$OR^4$ where $R^4$ is selected from hydrogen or alkyl of one to six carbon atoms, and (d) —$NR^5R^6$ where $R^5$ and $R^6$ are independently selected from hydrogen, alkyl of one to six carbon atoms, hydroxy, and alkoxy of one to six carbon atoms, or $R^5$ and $R^6$ taken together define a five- to eight-membered ring; with the proviso that $R^5$ and $R^6$ may not simultaneously be hydroxyl.

In those instances where M=OH, the compounds of the present invention are capable of forming base addition salts. In such instances, the term "pharmaceutically acceptable salts" refers to the relatively nontoxic inorganic and organic base addition salts of compounds of the present invention. These salts can be prepared in situ during the final isolation and purification of the compounds, or by separately reacting the purified carboxyl compound with a suitable base such as the hydroxide, carbonate, or bicarbonate of a pharmaceutically acceptable metal cation or with ammonia, or an organic primary, secondary, or tertiary amine of sufficient basicity to form a salt with the carboxyl functional group of the compounds of this invention.

Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. (See, for example. S. M. Berge, et al., J. Pharmaceutical Sciences, 1977, 66:1–19, which is incorporated herein by reference).

Similarly, in those instances where the compounds of the present invention possess a heterocyclic ting moiety containing a basic nitrogen atom, the compounds are capable of forming acid addition salts. In such cases, the term "pharmaceutically acceptable salts" refers to the relatively non-toxic inorganic and organic acid addition salts of compounds of the present invention. These salts can be prepared in situ during the final isolation and purification of the compounds, or by separately reacting the pitied compound in its free-base form with a suitable inorganic or organic acid and isolating the salt thus formed. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. (See, for example, S. M. Berge, et al., *J. Pharmaceutical Sciences*, 1977, 66:1–19, which is incorporated herein by reference). Said pharmaceutically acceptable acid and base addition salts are also contemplated as falling within the scope of the present invention.

The present invention also provides pharmaceutical compositions which comprise a therapeutically effective amount of compound as defined above in combination with a pharmaceutically acceptable carrier.

The invention further relates to a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms "alkoxy" and "alkoxyl" denote an alkyl group, as defined above, attached to the parent molecular moiety through an oxygen atom. Representative alkoxy groups include methoxy, ethoxy, propoxy, butoxy, and the like.

The terms "alkenyl" as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term "alkylene" denotes a divalent group derived from a straight or branched chain saturated hydrocarbon containing by the removal of two hydrogen atoms, for example —$CH_2$—, —$CH_2CH_2$—, —$CH(CH_3)CH_2$— and the like.

The term "cycloalkyl" as used herein refer to a monovalent saturated cyclic is hydrocarbon group. Representative cycloalkyl groups include cyclopropyl, cyclobutyl, cyclopentyl, cyclohexyl, cycloheptyl, bicyclo[2.2.1]heptane and the like.

"Cycloalkylene" denotes a divalent radical derived from a cycloalkane by the removal of two hydrogen atoms.

The term "phenylalkyl" refers to a phenyl group attached to the parent molecular moiety through an alkylene group. Representative phenylalkyl groups include phenylmethyl, phenylethyl, phenylpropyl, and the like.

The term "alkylphenyl" refers to an alkylene group attached to the parent molecular moiety through a phenyl group. Representative alkylphenyl groups include methylphenyl, ethylphenyl, propylphenyl, and the like.

The term "haloalkyl" denotes an alkyl group, as defined above, having one, two, or three halogen atoms attached thereto and is exemplified by such groups as chloromethyl, bromoethyl, trifluoromethyl, and the like.

As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups reactive with the carboxyl group of the compounds of this invention (where M is —OH) well known to practitioners of the art. They include, but are not limited to such groups as alkanoyl (such as acetyl, propionyl, butyryl, and the like), unsubstituted as and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs of other leukotriene biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

PREFERRED EMBODIMENTS

Compounds contemplated as falling within the scope of the present invention include, but are not limited to:

bis(4-(2-quinolyimethoxy)phenyl)methyloximinoacetic acid, bis(4-(2-quinolylmethoxy)phenyl)ketone oxime, bis(4-(2-quinolylmethoxy)phenylmethyloximinoacetic acid, ethyl ester, bis(4-(2-quinolylmethoxy)phenyl)methyloximinoacetic acid, sodium salt, bis(4-(6-fluoro-2-quinolyimethoxy)phenyl) methyloximinoacetic acid, bis(4-(7-chloro-2-quinolylmethoxy)phenyl) methyloximinoacetic acid, bis(4-(7-chloro-2-quinolyimethoxy)phenyl) methyloximinoacetic acid, sodium salt, bis(4-(2-benzothiazoylmethoxy)phenyl) methyloximinoacetic acid, bis(4-(2-benzothiazoylmethoxy)phenyl) methyloximinoacetic acid, sodium salt, bis(4-(2-pyridylmethoxy)phenyl)methyloximinoacetic acid, 3,3-bis((4-(2-quinolylmethoxy)phenyl)propenoic acid, 3,3-bis((4-(2-quinolylmethoxy)phenyl)-2-propen-1-yloximinoacetic acid, 3,3-bis((4-(2-quinolylmethoxy)phenyl)-2-propen-1-yloximinoacetic acid, sodium salt, bis(4-(2-quinoxalylmethoxy)phenyl)methyloximinoacetic acid, bis(4-(6-phenyl-2-pyridylmethoxy)phenyl) methyloximinoacetic acid, bis(4-(5-phenyl-2-pyridylmethoxy)phenyl) methyloximinoacetic acid, bis(4-(6-(pyrid-2-yl)-2-pyridylmethoxy )phenyl) methyloximinoacetic acid, bis(4-(2-benzoxazolylmethoxy)phenyl) methyloximinoacetic acid, bis(4-(1H- 1 -methyl-2-benzimidazolylmethoxy)phenyl )methyloximinoacetic acid, bis(4-(4-phenyl-2-pyrimidylmethoxy)phenyl) methyloximinoacetic acid, bis(4-(4-phenyl-2-thiazolylmethoxy)phenyl) methyloximinoacetic acid, and bis(4-(4-(pyrid-2-yl)-2-thiazolylmethoxy)phenyl) methyloximinoacetic acid.

Preferred compounds have the structure defined above wherein Z is selected from the group consisting of N—OH, N—O—A—COM, CH—COM, and CH—CH=N—O—A—COM, wherein A is alkylene of one to six carbon atoms; and M is —OH or a pharmaceutically acceptable salt of the carboxylate anion of M==—OH.

More preferred compounds of the present invention have the structure defined immediately above wherein W is selected from the group consisting of (a) quinolyl, (b) quinolyl substituted with (b-1) halogen, (b-2) alkyl of one to six carbon atoms, (b-3) phenyl, (b-4) phenyl substituted with halogen, alkyl of one to six carbon atoms, haloalkyl of one to six carbon atoms, or alkoxy of one to six carbon atoms, (b-5) pyridyl, or (b-6) pyridyl substituted with halogen, alkyl of one to six carbon atoms, or alkoxy of one to six carbon atoms, (c) benzothiazolyl, (d) benzothiazolyl substituted with (d-1) halogen, (d-2) alkyl of one to six carbon atoms, (d-3) phenyl, (d-4) phenyl substituted with halogen, alkyl of one to six carbon atoms, haloalkyl of one to six carbon atoms, or alkoxy of one to six carbon atoms, (d-5) pyridyl, or (d-6) pyridyl substituted with halogen, alkyl of one to six carbon atoms, or alkoxy of one to six carbon atoms.

Representative examples of more preferred compounds include, but are not limited to:

bis(4-(2-quinolylmethoxy)phenyl)methyloximinacetic acid,
bis(4-(2-quinolylmethoxy)phenyl)methyloximinoacetic acid,
bis(4-(2-quinolylmethoxy)phenyl)methyloximinacetic acid,
bis(4-(2-quinolylmethoxy)phenyl)methyloximinacetic acid, sodium salt,
bis(4-(6-fluoro-2-quinolylmethoxy)phenyl) methyloximinacetic acid,
bis(4-(7-chloro-2-quinolylmethoxy)phenyl) methyloximinacetic acid,
bis(4-(7-chloro-2-quinolylmethoxy)phenyl) methyloximinacetic acid, sodium salt,
bis(4-(2-benzothiazoylmethoxy)phenyl)methyloximinacetic acid,
bis(4-(2-benzothiazoylmethoxy)phenyl)methyloximinacetic acid, sodium salt,
bis(4-(2-pyridylmethoxy)phenyl)methyloximinacetic acid,
3,3-bis((4-(2-quinolylmethoxy)phenyl)propenoic acid,
3,3-bis((4-(2-quinolylmethoxy)phenyl)-2-propen-1-yloximinoacetic acid, and
3,3-bis((4-(2-quinolylmethoxy)phenyl)-2-propen-1-yloximinoacetic acid, sodium salt.

The most preferred compounds of the present invention have the structure defined immediately above wherein Z is selected from the group consisting of N—O—A—COM, and CH—CH=N—O—A—COM, wherein A is alkylene of one to six carbon atoms; and M is —OH or a pharmaceutically acceptable salt of the carboxylate anion of M=—OH.

Representative examples of the most preferred compounds include, but are not limited to 4-(2-quinolylmethoxy)phenyl)methyloximinacetic acid,
bis(4-(2-quinolylmethoxy)phenyl)methyloximinacetic acid, sodium salt,
bis(4-(6-fluoro-2-quinolylmethoxy)phenyl) methyloximinacetic acid,
bis(4-(7-chloro-2-quinolylmethoxy)phenyl) methyloximinacetic acid,
bis(4-(7-chloro-2-quinolylmethoxy)phenyl) methyloximinacetic acid, sodium salt,
bis(4-(2-benzothiazoylmethoxy)phenyl)methyloximinacetic acid,
bis(4-(2-benzothiazoylmethoxy)phenyl)methyloximinacetic acid, sodium salt,
3,3-bis((4-(2-quinolylmethoxy)phenyl)-2-propen-1-yloximinoacetic acid, and
3,3-bis( (4-( 2-quinolylmethoxy)phenyl)-2-propen-1-yloximinoacetic acid, sodium salt.

LIPOXYGENASE INHIBITION DETERMINATION

Inhibition of leukotriene biosynthesis was evaluated in vitro using an assay involving calcium ionophore-induced $LTB_4$ expressed in human polymorphonuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, CA) and centrifugated at 400×g for 40 minutes at 20° C. The PMNL was collected, erythrocytes lysed and washed 2× and suspended at $1.0 \times 10^7$ cells/mL in Earle's balanced salt solution with 17 mM Earle's HEPES. Aliquots of the cell suspension were preincubated with test compounds dissolved in DMSO (final concentration <2%) for 15 minutes and stimulated with calcium ionophore (final concentration 8.3 µM) for 10 min. at 37° C. Incubations were stopped with the addition of two volumes of ice-cold methanol followed by centrifuging the cell suspensions at 4° C. for 10 minutes at 450×g. The amount of $LTB_4$ in the methanol extract was analyzed by enzyme-linked immunoassay or by HPLC analysis.

The compounds of this invention inhibit leukotriene biosynthesis as shown by the data for representative examples in Table 1.

TABLE 1

In Vitro Inhibitory Potencies Against 5-Lipoxygenase From Stimulated $LTB_4$ Formation in Human Polymorphonuclear Leukocytes

| Example | $IC_{50}$ (µM) |
| --- | --- |
| 1 | 0.032 |
| 2 | 0.040 |
| 6 | 0.220 |
| 9 | 0.040 |
| 11 | 0.050 |
| 12 | 0.026 |

Inhibition of leukotriene biosynthesis in vivo was evaluated using the Ionophore A23187-Induced Rat Pleural Inflammation Model. Pleural inflammation was induced in male rats following the method of Rao, et al. (Rao, T. S., Currie, J. L., Shaffer, A. F., Isakson, P. C., Evaluation of 5-lipoxygenase Inhibitors, Zileuton, A-78773 and ICI D-2138 in an Ionophore (A-23187) Induced Pleural Inflammation Model in the Rat, *Life Sciences*, 53, 147 (1993)). Rats were dosed with experimental compounds in 0.2% methocel one hour prior to the intrapleural injection of the calcium ionophore, A23187. The rats where lightly anesthetized with Pentrane (Abbott Laboratories) and injected intrapleurally with 0.5 ml of 2% ethanol in injectable saline (Abbott Laboratories) containing 20 µg of A23187 (Cal BioChem-Novabiochem). Thirty minutes later the animals were euthanised and the pleural cavities lavaged with ice cold saline (Abbott Laboratories). The lavage fluid was then added to ice cold methanol (final methanol concentration 30%) to lyse cells and precipitate protein. Eicosanoids were determined by enzyme immunoassay by standard methods.

TABLE 2

In Vivo Leukotriene Inhibition in Rat Pleural Inflammation

| Example | % Inhibition (dose) |
| --- | --- |
| 12 | 60% at 3.0 mg/kg |

PHARMACEUTICAL COMPOSITIONS

The present invention also provides pharmaceutical compositions which comprise compounds of the present invention formulated together with one or more non-toxic pharmaceutically acceptable carders. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drag from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal or vaginal administration are preferably suppositories which can be prepared by mixing the compounds of this invention with suitable non-irritating excipients or carders such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33, et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g., two to four separate doses per day.

PREPARATION OF COMPOUNDS OF THIS INVENTION

In general, the compounds of this invention are synthesized by reaction schemes 1–4 as illustrated below. The preparation of compounds of the invention wherein Z is N—OH is outlined in Scheme 1. The commercially available starting material, 4,4'-dihydroxybenzophenone I is reacted with the requiste hetero-arylmethylhalide (W—CH$_2$X where X is Cl, Br, or I and W is defined above) in the presence of a suitable base such as potassium carbonate or cesium carbonate to provide the ketone II. The desired oxime compounds of Formula III are prepared by standard methods of oxime formation from ketones, for example by treatment with hydroxylamine hydrochoride and pyridine.

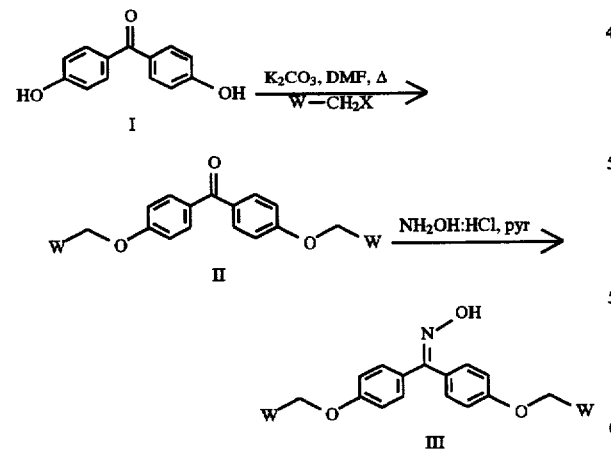

Compounds IV, wherein Z is N—O—A—COM, where A and M are defined above are prepared by reacting ketone intermediate II, prepared as described in Scheme 1, with the requisite hydroxylamine derivative NH$_2$—O—A—COM as shown in Scheme 2.

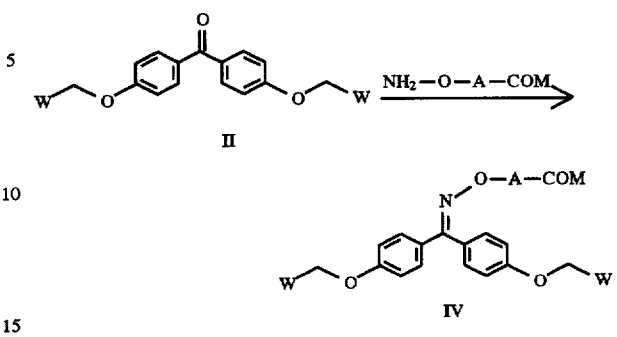

A general procedure for the synthesis of symmetrical unsaturated carboxylate derivatives wherein Z is CH—COM is outlined in Scheme 3. The ketone intermediate II is reacted with the lithiated enolate of ethyl trimethylsilylacetate in a Peterson olefination reaction to the form the intermediate ester which is saponified to provide the desired carboxylate of Formula V. The carboxylate function is then converted to the various derivatives defined by COM using known methods of the art. An alternative method for the olefination reaction with simple benzophenone using a Reformtsky-Peterson reaction which has been reported by Furstner in *J. Organomet. Chem.* 336(3), C33-6, (1987).

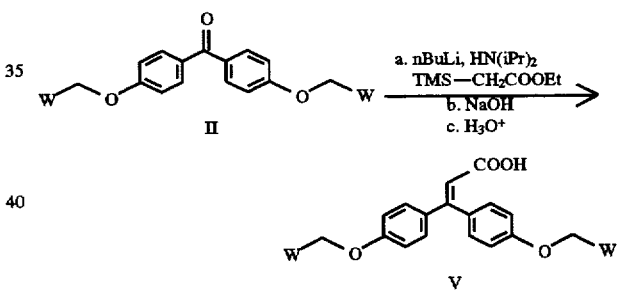

A general procedure for the synthesis of symmetrical unsaturated homologous oxime alkylcarboxylate derivatives, wherein Z is CH—CH=N—O—A—COM, is outlined in Scheme 4. The unsaturated carboxylate V, prepared as described in Scheme 3, is converted to the corresponding aldehyde intermediate VI by known methods, for example by reduction to the alcohol with lithium triethylborohydride and oxidation to the aldehyde using BaMnO$_4$. Aldehyde VI is then reacted with the requisite hydroxylamine derivative NH$_2$—O—A—COM to provide the desired unsaturated homologous O-substituted oxime derivatives of Formula VII.

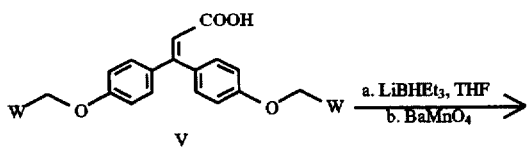

-continued
Scheme 4

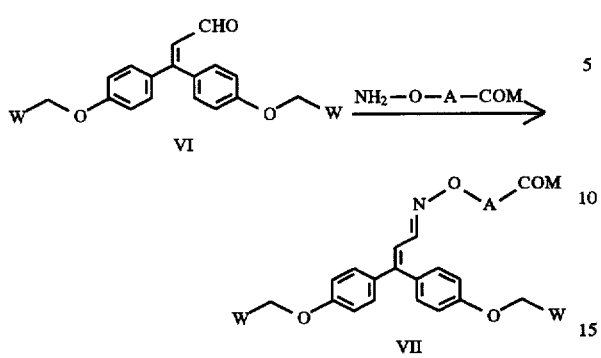

The foregoing may be better understood by reference to the following examples which are provided for illustration and not intended to limit the scope of the invention.

EXAMPLE 1

Preparation of bis(4-(2-quinolylmethoxy)phenyl) methyloximinoacetic acid

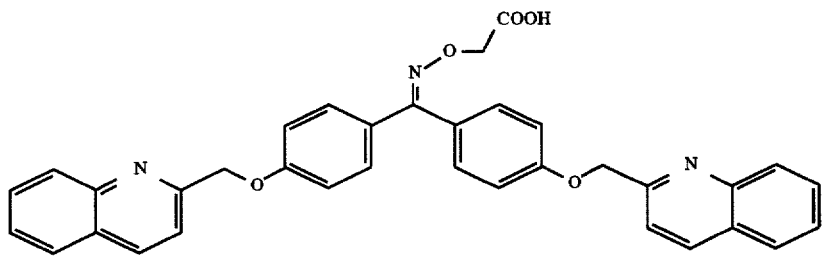

Step 1: bis(4-(2-quinolylmethoxy)phenyl) ketone

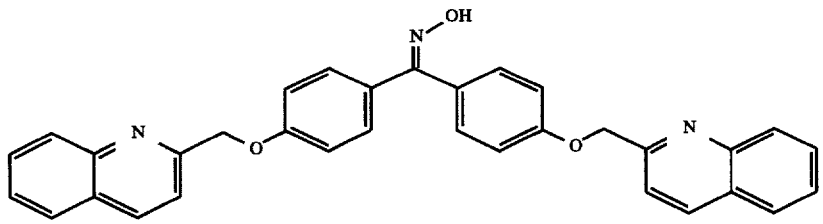

To a solution of 4-4'-dihydroxybenzophenone (4.22 g, 20 mmol) and $K_2CO_3$ (16.5 g, 120 mmol) in DMF (75 mL) was added 2-chloromethylquinoline hydrochloride (8.56 g, 40 mmol) and the resulting solution was stirred at 60° C. or 16 hours. The reaction mixture was then poured into ice water (100 mL and the resulting solid was collected by filtration, slurried in 20% ether/hexane, filtered, and dried in vacuo to afford bis(4-(2-quinolylmethoxy)phenyl) ketone (9.3 g, 94%) as white solid.

Step 2: bis(4-(2-quinolylmethoxy)phenyl) methyloximinoacetic acid

A mixture of bis(4-(2-quinolylmethoxyphenyl) ketone (1.25 g, 2.5 mmol), O-aminooxyacetic acid hydrochloride (564 mg, 2.5 mmol), sodium acetate (352 mg, 2.5 mmol) in $CH_3OH$ (40 mL), THF (10 mL) and water (5 mL) was refluxed for 4 days. The mixture was then concentrated in vacuo and the precipitated solid collected by filtration and recrystallized from $CH_2Cl_2$ to afford bis(4-(2-quinolylmethoxy)phenyl)-methyloximinoacetic acid (256 mg) as a white solid: mp 181°–183° C. (decomp); $^1$H NMR (300 MHz, DMSO-$d_6$)δ4.60 (s, 2H), 5.40 (s, 2H), 5.46 (s, 2H), 7.08 (d, 2H, J=9 Hz), 7.15 (d, 2H, J=9 Hz), 7.31 (d, 2H, J=9 Hz), 7.39 (d, 2H, J=9 Hz), 7.65 (m, 6H), 7.80 (m, 2H), 8.03 (m, 4H), 8.45 (t, 2H, J=9 Hz); MS (DCI/NH$_3$) m/e 570 (M+H)$^+$; Anal. Calcd. for $C_{35}H_{27}N_3O_5 \times 1/2$ $H_2O$: C, 72.64; H, 4.86; N, 7.27. Found: C, 72.34; H, 4.67; N, 7.07.

EXAMPLE 2

Preparation of bis(4-(2-quinolylmethoxy)phenyl) ketoxime

Step 1: bis(4-(2-quinolylmethoxy)phenyl) ketone

A mixture of 4,4'-dihydroxybenzophenone (12.4 g, 57.9 mmol), 2-chloromethylquinoline (23.4 g, 132 mmol) and cesium carbonate (46.0 g, 141.2 mmol) was stirred in dry DMF (170 mL). After 5 hours, saturated aqueous NaCl was added and the light brown solid formed was collected by filtration and washed with water. The solid was suspended in ether and collected by filtration, resuspended in ethanol and collected again by filtration and dried in vacuo to afford bis(4-(2-quinolylmethoxy)phenyl) ketone (27.3 g, 95%): IR (KBr) 1635, 1600, 1505, 1250 cm$^{-1}$; $^1$H NMR (300 MHz, DMSO-$d_6$)δ5.48 (s, 4H), 7.22 (d, 4H, J=9 Hz), 7.64 (m, 2H), 7.71 (d, 4H, J=9 Hz), 7.80 (m, 2H), 8.02 (m, 2H), 8.44 (d, 2H, J=8.5 Hz); MS (DCI/NH$_3$) m/e: 497 (M+H)$^+$.

Step 2: bis(4-(2-quinolylmethoxy)phenyl) ketoxime

To a stirred mixture of bis(4-(2-quinolylmethoxyphenyl) ketone (1.85 g, 3.72 mmol), hydroxylamine hydrochloride (1.80 g) and ethanol (100 mL) was added pyridine (5 mL) and the mixture was heated at reflux for 16 hours. The reaction mixture was cooled to ambient temperature and filtered, and the solid was washed with ethanol and dried in vacuo to afford bis(4-(2-quinolylmethoxy)phenyl) ketoxime (1.80 g, 95%): mp 198°–200° C.; IR (KBr) 3420, 3180, 1600, 1510, 1250 cm$^{-1}$; $^1$H NMR (300 MHz, DMSO-$d_6$) δ5.38 (s, 2H), 5.42 (s, 2H), 7.06 (d, 2H, J=8.8 Hz), 7.13 (d, 2H, J=8.8 Hz), 7.26 (d, 2H, J=8.8 Hz),7.32 (d, 2H, J=8.8 Hz), 7.62 (m, 2H), 7.69 (m, 2H), 7.80 (m, 2H), 8.02 (m, 4H), 8.43 (m, 2H), 11.10 (s, 1H).

EXAMPLE 3

Preparation of bis(4-(2-quinolylmethoxy)-phenyl) methyloximinoacetic acid ethyl ester To a stirred mixture in dry DMF (100 mL) of 4-(2-quinolylmethoxyphenyl) ketone oxime (7.6 g, 14.8 mmol), prepared as in Example 2, and cesium carbonate (6.1 g, 18.7 mmol) was added a solution of ethyl bromoacetate (3.2 g, 19.2 mmol) in dry DMF (25 mL). After stirring overnight, the resulting slurry was diluted with saturated aqueous NaCl and the white solid was collected by filtration, washed with water and dried to afford bis(4-(2-quinolylmethoxy)phenyl) methyloximinoacetic acid ethyl ester (8.7 g, 98%): IR (KBr) 1750, 1605, 1510, 1245, 1220 cm$^{-1}$;$^1$H NMR (300 MHz, DMSO-$d_6$)δ1.20 (t, 3H, J=7Hz), 4.14 (q, 2H, J=7 Hz), 5.40 (s, 2H), 5.43 (s, 2H), 7.09 (d, 2H, J=8.8 Hz), 7.16 (d, 2H, J=9 Hz), 7.30 (d, 2H, J=8.8 Hz), 7.37 (d, 2H, J=8.8 Hz), 7.63 (m, 2H), 7.69 (m, 2H), 7.80 (m, 2H), 8.01 (m, 4H), 8.43 (m, 2H).

EXAMPLE 4

Preparation of bis(4-(2-quinolylmethoxy) phenyl) methyloximinoacetic acid sodium salt quinolylmethoxy)phenyl)-methyloximinoacetic acid ethyl ester (8.5 g, 14.2 mmol), prepared as in Example 3, in THF (80 mL) and ethanol (10 mL). The turbid reaction was stirred for 1 hour, and then was diluted with water (80 mL). The aqueous layer was washed with 1:1 ether-hexane (50 mL) and then filtered to remove fine solids. The filtrate was acidified to pH 4 with 1N HCl, and the precipitated solid collected by filtration and dried in vacuo to give bis(4-(2-quinolylmethoxy)phenyl)methyloximinoacetic acid (6.9 g, 85%): mp 183°–185° C.

Step 2: bis(4-(2-quinolylmethoxy)phenyl) methyloximinoacetic acid sodium salt

A mixture of bis(4-(2-quinolylmethoxy)phenyl) methyloximinoacetic acid (570 mg, 1.00 mmol), prepared as in step 1, ethanol (7 mL), dry THF (3 mL), and 1N NaOH (1.10 mL, 1.10 mmol) was stirred for 1 hour. The reaction mixture was diluted with water and the aqueous phase was washed with hexane and concentrated in vacuo. The resulting solid was collected by filtration to provide bis(4-(2-quinolylmethoxy)phenyl)methyloximinoacetic acid sodium salt (0.48 g, 81%): $^1$H NMR (300 MHz, DMSO-$d_6$)δ4.18 (s, 2H), 5.38 (s, 2H), 5.42 (s, 2H), 7.05 (d, 2H, J=8.8 Hz), 7.10 (d, 2H, J=8.8 Hz), 7.29 (d, 2H, J=8.8 Hz), 7.29 (d, 2H, J=8.8 Hz), 7.57 (d, 2H, J=8.8 Hz), 7.62 (m, 2H), 7.69 (m, 2H), 7.79 (m, 2H), 8.02 (m, 2H), 8.43 (m, 2H); MS (FAB$^+$) m/z: 592 (M+H)$^+$. Anal. Calcd. for $C_{33}H_{26}N_3O_5$Na: C, 69.83; H, 4.61; N, 7.40. Found: C, 68.77; H, 4.29; N, 6.74.

EXAMPLE 5

Preparation of bis(4-(6-fluoro-2-quinolylmethoxy) phenyl)methyloximinoacetic acid

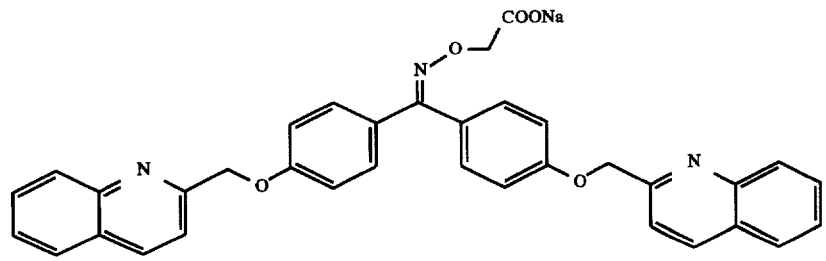

Step 1: bis(4-(2-quinolylmethoxy)phenyl) methyloximinoacetic acid

Lithium hydroxide monohydrate (1.4 g, 33.4 mmol) in 1:1 water-ethanol (20 mL) was added a solution of bis(4-(2-

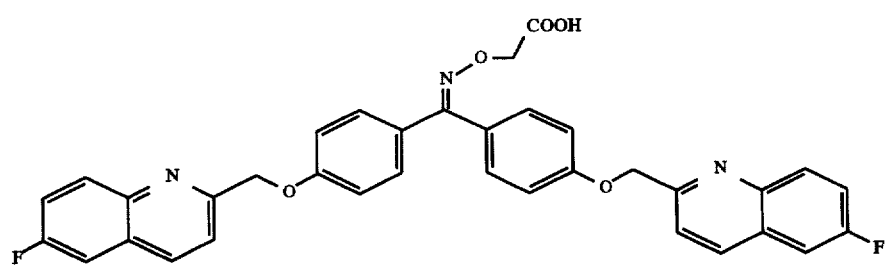

The desired product was prepared according to the procedure of Example 1, except substituting 2-bromomethyl-6-fluoroquinoline for 2-chloromethylquinoline: mp 107° C.; ¹H NMR (300 MHz, DMSO-d₆)δ4.55 (s, 2H), 5.36 (s, 2H), 5.45 (s, 2H), 7.08 (d, 2H, J=9 Hz), 7.14 (d, 2H, J=9 Hz), 7.32 (d, 2H, J=9 Hz), 7.42 (d, 4H, J=9 Hz), 7.78 (m, 6H), 8.11 (m, 2H,), 7.44 (t, 2H, J=9 Hz); MS (DCI/NH₃) m/e 606 (M+H)⁺. Anal. Calcd. for $C_{35}H_{25}F_2N_3O_5 \times H_2O$: C, 67.47; H, 4.35; N, 6.45. Found: C, 67.42; H, 4.36; N, 6.35.

EXAMPLE 6

Preparation of bis(4-(7-chloro-2-quinolylmethoxy)phenyl)methyloximinoacetic acid

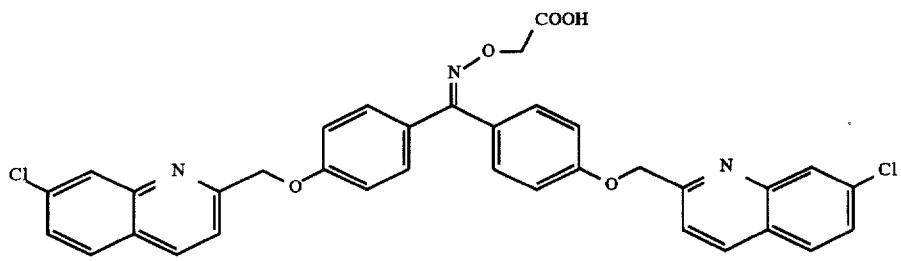

Step 1: bis(4-hydroxyphenyl)methyloximinoacetic acid ethyl ester

To a solution in dioxane/EtOH/H₂O (3:2:1, 70 mL) of 4,4'-dihydroxy-benzophenone (3.21 g, 15 mmol) was added aminooxyacetic acid hydrochloride (3.25 g, 15 mmol) and acetic acid (0.5 mL). The mixture was refluxed for 18 hours, cooled to room temperature, and concentrated in vacuo. The residue was diluted with CH₂Cl₂ (100 mL), washed with saturated aqueous of NaHCO₃ and brine, dried over MgSO₄, filtered, and concentrated in vacuo. Chromatography on silica gel (hexanes/EtOAC 1: 1 ) provided bis(4-hydroxyphenyl)methyloximinoacetic acid ethyl ester (2.4 g).

Step 2: bis(4-(7-chloro-2-quinolylmethoxy)-phenyl) methyloximinoacetic acid ethyl ester To a solution in dry DMF (20 mL) of bis(4-hydroxyphenyl)methyloximinoacetic acid ethyl ester (0.64 g, 2 mmol), prepared as in step 1, was added cesium carbonate (1.6 g, 5 mmol), the mixture was stirred for 10 mutes, and 2-bromomethyl-7-chloroquinoline (1 g, 4 mmol) was added. After stirring for 18 hours, the mixture was poured into water and the precipitated solid was collected by filtration, washed with water, and dried in vacuo. Chromatography on silica gel (hexane/EtOAC 3:1) afforded bis(4-(7-chloro-2-quinolylmethoxy)phenyl)-methyloximinoacetic acid ethyl ester (1.1 g).

Step 3: bis(4-(7-chloro-2-quinolylmethoxy)phenyl) methyloximinoacetic acid

To a solution in THF/EtOH/H₂O (3:2:1, 35 mL) of bis(4-(7-chloro-2-quinolylmethoxy)phenyl) methyloximinoacetic acid ethyl ester (0.66 g, 1 mmol), prepared as in step 2, was added aqueous 1N NaOH (5 mL. The mixture was stirred at room temperature for 18 hours, concentrated in vacuo, diluted with water, and neutralized with 6N HCl. The precipitated solid was collected by filtration and slurried in Et₂O/hexane (1:1, 50 mL), filtered, and dried in vacuo to provide bis(4-(7-chloro-2-quinolylmethoxy)phenyl)methyloximinoacetic acid (435 mg): mp 201°- 202° C.; ¹H NMR (300 MHz, DMSO-d₆) δ4.55 (s, 2H), 5.39 (s, 2H), 5.44 (s, 2H), 7.08 (d, 2H, J=9 Hz), 7.15 (d, 2H, J=9 Hz), 7.31 (d, 2H, J=9 Hz), 7.41 (d, 2H, J=9 Hz), 7.68 (m, 3H), 7.72 (d, 1H, J=9 Hz), 8.80 (m, 4H), 8.49 (t, 2H, J=9 Hz); MS (DCI/NH₃) m/e 638 (M+H)⁺. Anal. Calcd. for $C_{35}H_{25}Cl_2N_3O_5 \times H_2O$: C, 64.12; H, 4.12; N, 6.41. Found C, 64.44; H, 3.96; N, 6.30.

EXAMPLE 7

Preparation of bis(4-(7-chloro-2-quinolylmethoxy)-phenyl)methyloximinoacetic acid sodium salt To a solution in EtOH—THF (3:1, 4 mL) of bis(4-(7-chloro-2-quinolyl-methoxy)phenyl)methyloximinoacetic acid (240 mg, 0.4 mmol), prepared as in Example 5, was added 1N aqueous NaOH (0.5 mL, 0.5 mmol). The mixture was stirred overnight at room temperature and concentrated in vacuo. The residue was slurried in ether (15 mL), filtered, and dried in vacuo to provide bis(4-(7-chloro-2-quinolylmethoxy)phenyl)methyloximinoacetic acid sodium salt (220 mg): mp 181°-183° C.; ¹H NMR (300 MHz, DMSO-d₆)δ4.15 (s, 2H), 5.41 (m, 4H), 7.07 (dd, 4H, J=12, 3 Hz), 7.28 (d, 2H, J=9 Hz), 7.56 (d, 2H, J=9 Hz), 7.73 (m, 4H), 8.06 (m, 4H), 8.49 (m, 2H); MS (FAB) 660 (M+H)⁺, 682 (M+Na)⁺. Anal. Calcd. for $C_{35}H_{24}Cl_2N_3O_5Na \times 2.5 H_2O$: C, 59.58, H, 4.11; N, 5.96. Found C, 59.61; H, 3.94; N, 5.72.

EXAMPLE 8

Preparation of bis(4-(2-benzothiazoylmethoxy)phenyl)methyloximinoacetic acid

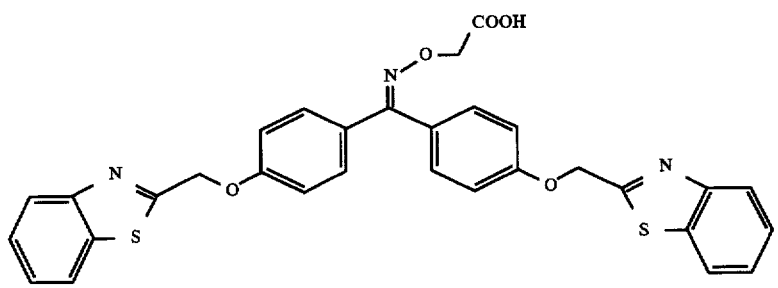

The desired product was prepared according to the procedure of Example 5, except substituting 2-chloromethylbenzothiazole for 2-bromomethyl-7-chloroquinoline: mp 205°–207° C.; $^1$H NMR (300 MH$_z$, DMSO-d$_6$)δ4.6 (s, 2H), 5.63 (s, 2H), 5.68 (s, 2H), 7.13 (d, 2H, J=9 Hz), 7.20 (d, 2H, J=9 Hz), 7.33 (d, 2H, J=9 Hz), 7.41 (d, 2H, J=9 Hz) 7.60 (m, 4H), 8.04 (m, 2H), 8.14 (m, 2H); MS (DCI/NH$_3$) m/e 582 (M+H)$^+$, 599 (M+NH$_4$)$^+$. Anal. Calcd for C$_{31}$H$_{23}$N$_3$O$_5$S$_2$×H$_2$O: C, 62.15; H, 4.12; N, 6.94. Found: C, 62.10; H, 4.21; N, 7.01.

EXAMPLE 9

Preparation of bis(4-(2-benzothiazoylmethoxy)phenyl)methyloximinoacetic acid sodium salt The desired salt of the product of Example 8 was prepared according to the procedure of Example 7, except substituting bis(4-(2-benzothiazoylmethoxy) -phenyl) methyloximinoacetic acid, prepared as in Example 8, for 4-(7-chloro-2-quinolylmethoxyphenyl) ketone oxime-O-acetic acid. $^1$H NMR (300 MHz, DMSO-d$_6$)δ4.16 (s, 2H), 5.63 (s, 2H), 5.67 (s, 2H), 7.11 (m, 4H), 7.31 (m, 2H), 7.53 (m, 6H), 8.03 (m, 2H), 8.14 (m, 2H); MS (FAB)$^+$604 (M+H)$^+$, 626 (M+Na)$^+$. Anal. Calcd. for C$_{31}$H$_{22}$N$_3$O$_5$S$_2$Na× 2H$_2$O: C, 58.21; H, 4.07; N,6.57. Found C, 58.52; H, 3.94; N, 6.40.

EXAMPLE 10

Preparation of bis(4-(2-pyridylmethoxy)phenyl) methyloximinoacetic acid

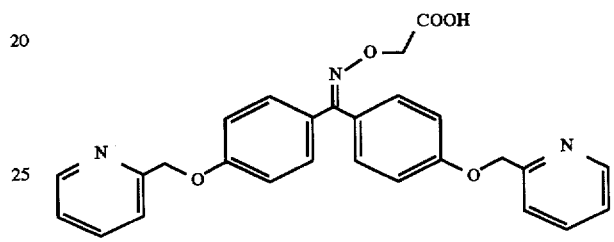

The desired material was prepared according to the procedure of Example 1, except substituting 2-picolylchloride for 2-chloromethylquinoline: mp 154° C.; $^1$H NMR (300 MHz, DMSO-d$_6$)δ4.60 (s, 2H), 5.18 (s, 2H), 5.24 (s, 2H), 7.04 (d, H, J=9 Hz), 7.12 (d, 4H, J=9 Hz), 7.34 (m, 6H), 7.52 (m, 2H), 7.85 (m, 2H), 8.57 (m, 2H); MS (DCI/NH$_3$) m/e 470 (M+H)$^+$. Anal. Calc'd. for C$_{27}$H$_{23}$N$_3$O$_5$×1/2 H$_2$O: C, 67.77; H, 5.06; N, 8.58. Found: C, 67.63; H, 5.22; N, 8.33.

EXAMPLE 11

Preparation of 3,3-bis((4-(2-quinolylmethoxy) phenyl)propenoic acid

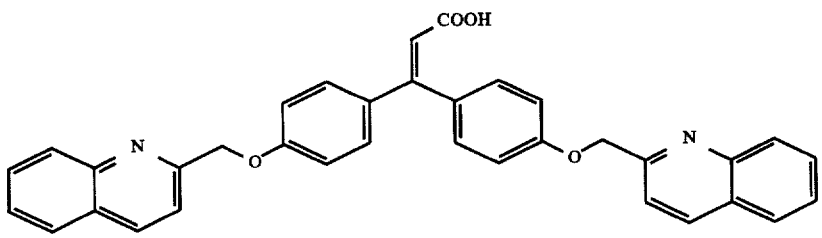

Step 1: 3,3-bis((4-(2-quinolylmethoxy)phenyl)propenoic acid ethyl ester

To −78° C. mixture of diisopropylamine (400 mg, 4 mmol) and THF (20 mL) was added n-BuLi (1.6 mL, 4.0 mmol) and the mixture was stirred for 15 min. Ethyltrimethylsilylacetate (640 mg, 4 mmol) was added dropwise and the mixture was stirred for 15 min. To this mixture was added dropwise over 15 minutes a solution of 4-(2-quinolylmethoxy)phenyl ketone (1.0 g, 2 mmol) in dry THF (25 mL). The mixture was stirred for 30 minutes at −78° C., allowed to warm to room temperature over 30 mutes and quenched by adding KHSO₄ (750 mg) followed by water (50 mL). The mixture was extracted with ether (100 mL), washed with brine, dried over MgSO₄, filtered, and concentrated in vacuo. Chromatography on silica gel (9:1 CH₂Cl₂/EtOAC) gave 3,3-bis((4-(2-quinolylmethoxy)phenyl)-propenoic acid ethyl ester (920 mg, 82%) as white solid: mp 122°–123° C.

Step 2: 3,3-bis((4-(2-quinolylmethoxy)phenyl)propenoic acid

To a solution in hot ethanol of 3,3-bis((4-(2-quinolylmethoxy)phenyl)-propenoic acid ethyl ester (560 mg, 1 mmol), prepared as in step 1, was added aqueous 1N NaOH (8 mL) and the reaction mixture was heated at reflux for 3 hours. The reaction mixture was cooled to room temperature, concentrated in vacuo, diluted with water (25 mL), and neutralized with 10% citric acid solution. The resulting precipitate was collected by filtration, washed with water, slurried in warm EtOH (20 mL), collected by filtration, and dried in vacuo to obtain 3,3-bis((4-(2-quinolyl-methoxy)phenyl)propenoic acid (265 mg): mp 127°–130° C.; $^1$H NMR (300 MHz, DMSO-d₆)δ5.40 (s, 4H), 6.20 (s, 1H), 7.08 (m, 6H), 7.21 (d, 2H, J=9 Hz), 7.73 (m, 6H), 8.03 (m, 4H), 8.44 (t, 2H, J=9 Hz), 11.97 (bs, 1H); MS (DCI/NH₃) m/e 538 (M+H)⁺. Anal. Calcd. for C₃₅H₂₆N₃O₅×3H₂O: C, 70.95; H, 5.41; N, 4.73. Found: C, 70.53; H, 5.24; N, 4.61.

EXAMPLE 12

Preparation of 3,3-bis((4-(2-quinolylmethoxy) phenyl)-2-propen-1-yloximinoacetic acid

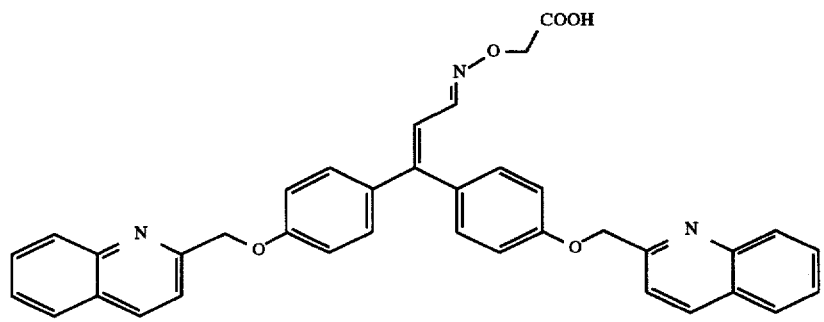

Step 1: 3,3-bis((4-(2-quinolylmethoxy)phenyl)propen-1-ol

To a −23° C. (CCl₄-dry ice) solution in dry THF (25 mL) of 3,3-di-4-(2-quinolylmethoxyphenyl) propenoic acid ethyl ester (1.1 g, 2 mmol), prepared as in Example 10, was added lithium triethylborohydride (4 mL of 1.0M solution, 4 mmol) slowly under N₂. The reaction mixture was stirred for 1 hour, quenched with aqueous saturated NH₄Cl, and extracted with Et₂O (100 mL). The organic layer was washed with brine, dried over MgSO₄, filtered, and concentrated in vacuo. Chromatography on silica gel (3% CH₃OH—CH₂Cl₂) provided 3,3-bis((4-(2-quinolylmethoxy)phenyl)propen-1-ol (530 mg) as yellow oil.

Step 2: 3,3-bis((4-(2-quinolylmethoxy)phenyl)propenal

To a solution in toluene of 3,3-bis((4-(2-quinolylmethoxy)phenyl)propen-1-ol (520 mg, 1 mmol), prepared as in step 1 was added BaMnO₄ (2.56 g, 10 mmol) and reaction was stirred for 3 hours under N₂. The mixture was filtered through a celite pad and the filtrate was concentrated in vacuo to provide 3,3-bis((4-(2-quinolylmethoxy)phenyl)propenal (520 mg) as yellow oil which was used in the next step without further purification.

Step 3: 3,3-bis((4-(2-quinolylmethoxy)phenyl)-2-propen-1-yloximinoacetic acid

The desired product was prepared according to the procedure of Example 1, step 2, except substituting the 3,3-bis ((4-(2-quinolylmethoxy)phenyl)propenal prepared in step 2 for 4-(2-quinolylmethoxyphenyl) ketone: mp 125°–127° C.; $^1$H NMR (300 MHz, DMSO-d₆)δ4.51 (s, 2H), 5.40 (s, 2H), 5.45 (s, 2H), 6.68 (d, 1H, J=9 Hz), 7.15 (m, 6H), 7.7 (m, 7H), 8.02 (m, 4H), 8.45 (t, 2H, J=9 Hz), 12.75 (bs, 1H); MS (DCI/NH₃) m/e 596 (M+H)⁺. Anal. Calcd. for C₃₇H₂₉N₃O₅× 1.5 H₂O: C, 71.31; H, 5.14; N, 6.75. Found: C, 71.61; H, 5.04; N, 6.67.

EXAMPLE 13

Preparation of 3,3-bis((4-(2-quinolylmethoxy)- phenyl)-2-propen-1-yloximinoacetic acid sodium salt The desired compound is prepared according to the method of Example 7, except substituting 3,3-bis((4-(2-quinolylmethoxy)phenyl)-2-propen- 1 -yloximinoacetic acid, prepared as in Example 12, for bis(4-(7-chloro-2-quinolylmethoxy)-phenyl)methyliminoxyacetic acid.

The examples shown below are prepared in a manner analogous to that of Example 1, except substituting the requisite heteroarylmethylchloride for 2-chloromethylquinoline. The requiste heteroarylmethyl-chlorides are prepared by literature methods.

EXAMPLE 14 bis(4-(2-quinoxalylmethoxy)phenyl) methyliminoxyacetic acid

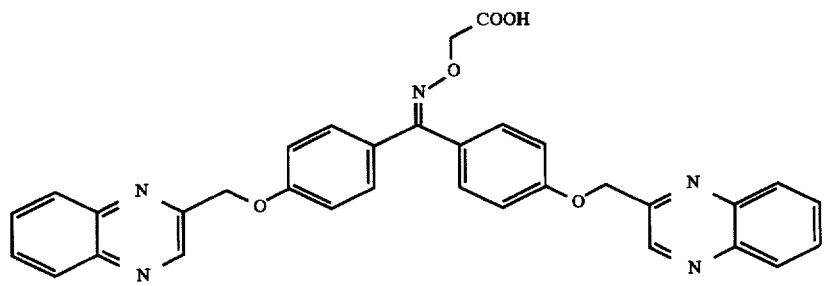
EXAMPLE 15
bis(4-(6-phenyl-2-pyridylmethoxy)phenyl)
methyliminoxyacetic acid
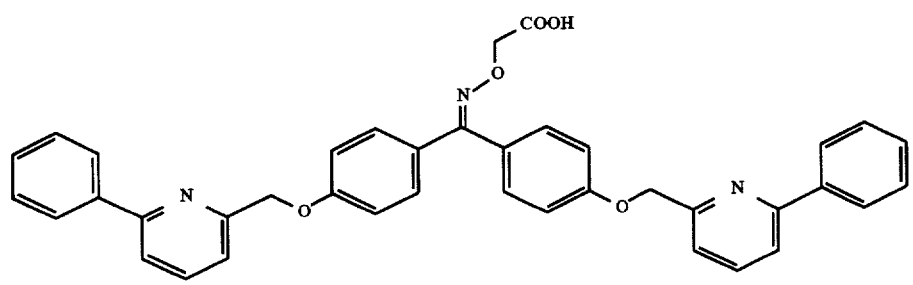
EXAMPLE 16
bis(4-(5-phenyl-2-pyridylmethoxy)phenyl)
methyliminoxyacetic acid
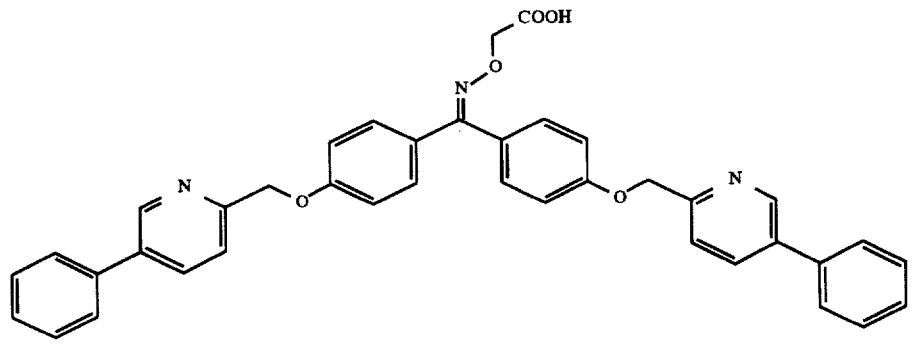
EXAMPLE 17
bis(4-(6-(pyrid-2-yl)-2-pyridylmethoxy)phenyl)
methyliminoxyacetic acid

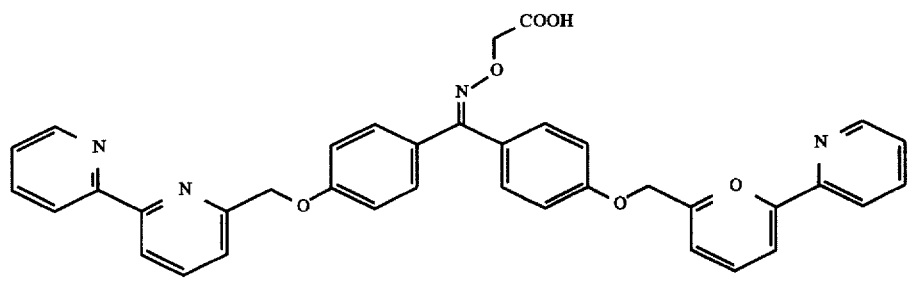
EXAMPLE 18
bis(4-(2-benzoxazolylmethoxy)phenyl)
methyliminoxyacetic acid
EXAMPLE 21
bis(4-(4-phenyl-2-thiazolylmethoxy)phenyl)
methyliminoxyacetic acid
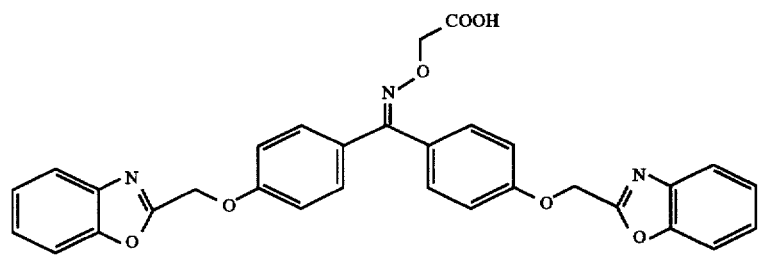
EXAMPLE 19
bis(4-(1H-1-methyl-2-benzimidazolylmethoxy)
phenyl)methyliminoxyacetic acid
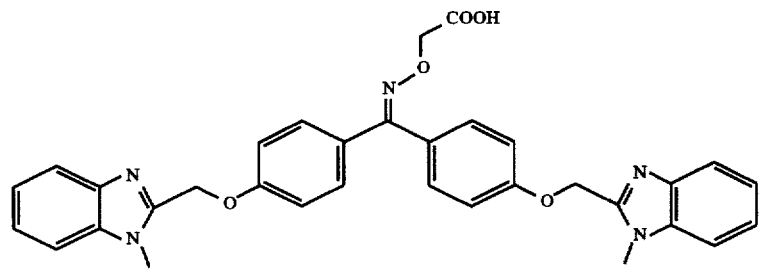
EXAMPLE 20
bis(4-(4-phenyl-2-pyrimidylmethoxy)phenyl)
methyliminoxyacetic acid
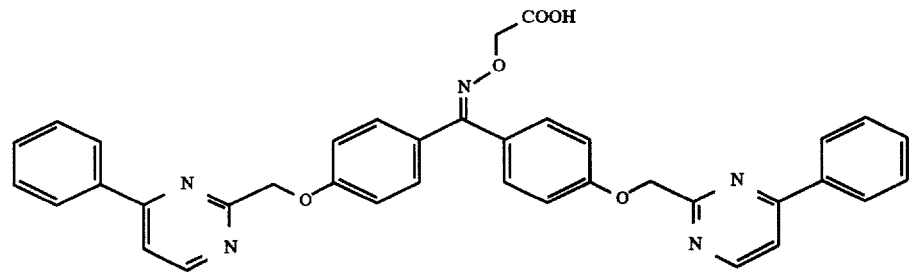

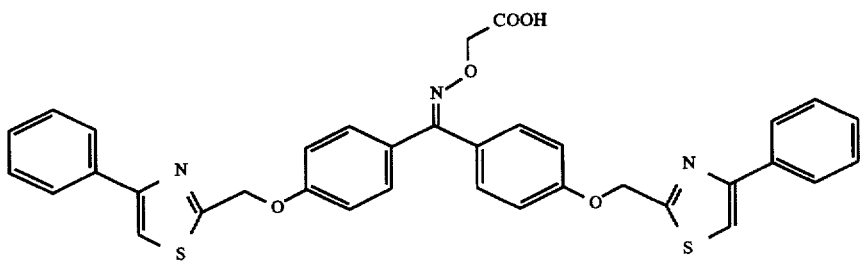

EXAMPLE 22 bis(4-(4-(pyrid-2-yl)-2-thiazolylmethoxy)phenyl)
methyliminoxyacetic acid

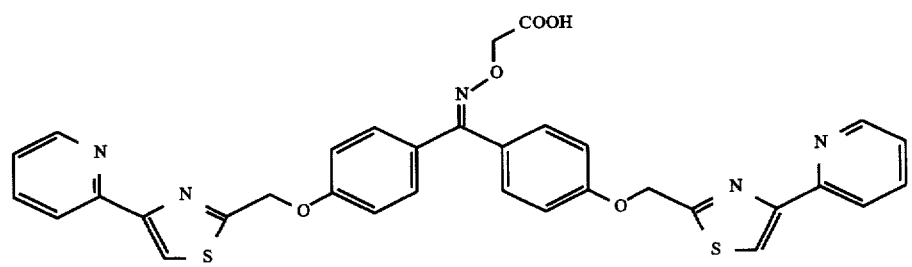

The foregoing examples are merely illustrative of the invention and are not intended to limit the invention to the disclosed compounds. Variations and changes which are obvious to one skilled in the art are intended to be within the scope and nature of the invention which is defined in the appended claims.

What is claimed is:

1. A compound of formula:

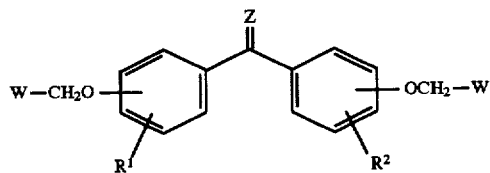

or a pharmaceutically acceptable salt thereof;
wherein W is the same at each occurrence and is selected from the group consisting of:
(a) quinolyl;
(b) quinolyl substituted with a substituent selected from the group consisting of
halogen,
alkyl of one to six carbon atoms,
phenyl,
phenyl substituted with a substituent selected from the group consisting of
halogen,
alkyl of one to six carbon atoms,
haloalkyl of one to six carbon atoms, and
alkoxy of one to six carbon atoms;
pyridyl; and
pyridyl substituted with a substituent selected from
halogen,
alkyl of one to six carbon atoms, and
alkoxy of one to six carbon atoms;
(c) quinoxalyl;
(d) quinoxalyl substituted with a substituent selected from
halogen, and
alkyl of one to six carbon atoms;
(e) pyridyl;
(f) pyridyl substituted with a substituent selected from the group consisting of
phenyl,
phenyl substituted with a substituent selected from
halogen,
alkyl of one to six carbon atoms,
haloalkyl of one to six carbon atoms, and
alkoxy of one to six carbon atoms,
pyridyl, and
pyridyl substituted with a substituent selected from
halogen,
alkyl of one to six carbon atoms, and
alkoxy of one to six carbon atoms;
(g) pyrimidyl;
(h) pyrimidyl substituted with a substituent selected from
phenyl,
phenyl substituted with a substituent selected from
halogen,
alkyl of one to six carbon atoms,
haloalkyl of one to six carbon atoms, and
alkoxy of one to six carbon atoms,
pyridyl, and
pyridyl substituted with a substituent selected from
halogen,
alkyl of one to six carbon atoms, and
alkoxy of one to six carbon atoms;
$R^1$ and $R^2$ are independently selected from the group consisting of:
(a) hydrogen,
(b) alkyl of one to six carbon atoms,
(c) halolalkyl of one to six carbon atoms,
(d) alkoxy of one to six carbon atoms, and
(e) halogen;
Z is selected from the group consisting of:

(a) N—OH,
(b) N—O—A—COM,
(c) CH—COM, and
(d) CH—CH=N—O—A—COM;

A is selected from the group consisting of:
(a) alkylene of one to six carbon atoms,
(b) alkenylene of two to six carbon atoms,
(c) cycloalkylene of three to eight carbon atoms,
(d)

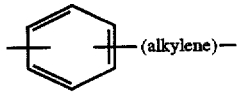

wherein the alkylene portion is of one to six carbon atoms,
(e)

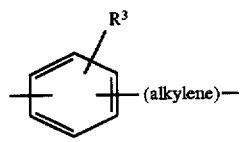

wherein the alkylene portion is of one to six carbon atoms, and $R^3$ is selected from the group consisting of halogen, alkyl of one to six carbon atoms, and haloalkyl of one to six carbon atoms,
(f)

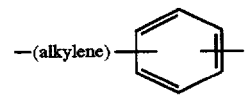

wherein the alkylene portion is of one to six carbon atoms, and
(g)

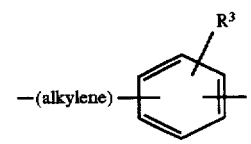

wherein the alkylene portion is of one to six carbon atoms and $R^3$ is as defined above;

M is selected from the group consisting of:
(a) a pharmaceutically acceptable cation,
(b) a pharmaceutically acceptable metabolically cleavable group,
(c) —$OR^4$ where $R^4$ is selected from the group consisting of hydrogen and alkyl of one to six carbon atoms, and
(d) —$NR^5R^6$ where $R^5$ and $R^6$ are independently selected from hydrogen, alkyl of one to six carbon atoms, hydroxy, and alkoxy of one to six carbon atoms, with the proviso that $R^5$ and $R^6$ may not simultaneously be hydroxyl.

2. A compound as defined by claim 1, or a pharmaceutically acceptable salt thereof wherein Z is selected from the group consisting of:
N—OH,
N—O—A—COM,
CH—COM, and
CH—CH=N—O—A—COM, wherein A is alkylene of one to six carbon atoms; and M is —OH.

3. A compound as defined by claim 2 wherein W is selected from the group consisting of:
pyridyl,
pyridyl substituted with
  phenyl,
  phenyl substituted with
    halogen,
    alkyl of one to six carbon atoms,
    haloalkyl of one to six carbon atoms, or
    alkoxy of one to six carbon atoms,
  pyridyl, or
  pyridyl substituted with
    halogen,
    alkyl of one to six carbon atoms, or
    alkoxy of one to six carbon atoms,
pyrimidyl,
pyrimidyl substituted with
  phenyl,
  phenyl substituted with
    halogen,
    alkyl of one to six carbon atoms,
    haloalkyl of one to six carbon atoms, or
    alkoxy of one to six carbon atoms,
  pyridyl, or
  pyridyl substituted with
    halogen,
    alkyl of one to six carbon atoms, or
    alkoxy of one to six carbon atoms.

4. A compound as defined by claim 2 wherein W is selected from the group consisting of:
quinolyl,
quinolyl substituted with
  halogen,
  alkyl of one to six carbon atoms,
  phenyl,
  phenyl substituted with
    halogen,
    alkyl of one to six carbon atoms,
    haloalkyl of one to six carbon atoms, or
    alkoxy of one to six carbon atoms,
  pyridyl, or
  pyridyl substituted with
    halogen,
    alkyl of one to six carbon atoms, or
    alkoxy of one to six carbon atoms,
quinoxalyl, and
quinoxalyl substituted with
  halogen, or
  alkyl of one to six carbon atoms.

5. A compound as defined by claim 2 wherein W is selected from the group consisting of:
quinolyl,
quinolyl substituted with
  halogen,
  alkyl of one to six carbon atoms,
  phenyl,
  phenyl substituted with
    halogen,
    alkyl of one to six carbon atoms,
    haloalkyl of one to six carbon atoms, or
    alkoxy of one to six carbon atoms,
  pyridyl, or
  pyridyl substituted with
    halogen,
    alkyl of one to six carbon atoms, or
    alkoxy of one to six carbon atoms.

6. A compound as defined by claim 5, or a pharmaceutically acceptable salt thereof wherein Z is selected from the group consisting of:

N—O—A—COM, and

CH—CH=N—O—A—COM, wherein A is alkylene of one to six carbon atoms; and M is —OH.

7. A compound or pharmaceutically acceptable salt thereof as defined by claim 1 selected from the group consisting of:

bis(4-(2-quinolylmethoxy)phenyl)methyloximinoacetic acid, bis(4-(2-quinolylmethoxy)phenyl)ketone oxime, bis(4-(2-quinolylmethoxy)phenylmethyloximinoacetic acid, ethyl ester, bis(4-(2-quinolylmethoxy)phenyl)methyloximinoacetic acid, sodium salt, bis(4-(6-fluoro-2-quinolylmethoxy)phenyl) methyloximinoacetic acid, bis(4-(7-chloro-2-quinolylmethoxy)phenyl) methyloximinoacetic acid, bis(4-(7-chloro-2-quinolylmethoxy)phenyl) methyloximinoacetic acid, sodium salt, bis(4-(2-pyridylmethoxy)phenyl)methyloximinoacetic acid, 3,3-bis((4-(2-quinolylmethoxy)phenyl)propenoic acid, 3,3-bis((4-(2-quinolylmethoxy)phenyl)-2-propen-1-yloximinoacetic acid, 3,3-bis((4-(2-quinolylmethoxy)phenyl)-2-propen-1-yloximinoacetic acid, sodium salt.

8. A compound or pharmaceutically acceptable salt thereof as defined by claim 1 selected from the group consisting of:

bis(4-(2-quinolylmethoxy)phenyl)methyloximinacetic acid, bis(4-(2-quinolylmethoxy)phenyl)methyloximinacetic acid, sodium salt, bis(4-(6-fluoro-2-quinolylmethoxy)phenyl) methyloximinacetic acid, bis(4-(7-chloro-2-quinolylmethoxy)phenyl) methyloximinacetic acid, bis(4-(7-chloro-2-quinolylmethoxy)phenyl) methyloximinacetic acid, sodium salt, 3,3-bis((4-(2-quinolylmethoxy)phenyl)-2-propen-1-yloximinoacetic acid, and 3,3-bis((4-(2-quinolylmethoxy)phenyl)-2-propen-1-yloximinoacetic acid, sodium salt.

9. A method for inhibiting lipoxygenase activity or leukotriene biosynthesis in a mammal in need of such treatment comprising administering to the mammal a therapeutically effective amount of a compound of claim 1.

10. A composition for inhibiting lipoxygenase activity or the biosynthesis of leukotrienes comprising a pharmaceutical carrier and a therapeutically effective amount of a compound of claim 1.

* * * * *